US008915944B2

(12) United States Patent
Pisharodi (10) Patent No.: US 8,915,944 B2
(45) Date of Patent: Dec. 23, 2014

(54) ROD AND PLATE SYSTEM FOR INCREMENTAL REDUCTION OF THE SPINE

(75) Inventor: Madhavan Pisharodi, Brownsville, TX (US)

(73) Assignee: Perumala Corporation, Brownsville, TX (US)

( * ) Notice: Subject to any disclaimer, the term of this patent is extended or adjusted under 35 U.S.C. 154(b) by 359 days.

(21) Appl. No.: 13/065,796

(22) Filed: Mar. 30, 2011

(65) Prior Publication Data

US 2011/0245877 A1  Oct. 6, 2011

Related U.S. Application Data

(63) Continuation-in-part of application No. 12/148,006, filed on Apr. 15, 2008, now abandoned.

(51) Int. Cl.
*A61B 17/70* (2006.01)

(52) U.S. Cl.
CPC ......... *A61B 17/7037* (2013.01); *A61B 17/7007* (2013.01); *A61B 17/7041* (2013.01); *A61B 17/7001* (2013.01)
USPC ............ 606/264; 606/246; 606/267; 606/300

(58) Field of Classification Search
USPC ................................. 606/246–279, 300–321
See application file for complete search history.

(56) References Cited

U.S. PATENT DOCUMENTS

| 2007/0149973 A1* | 6/2007 | Clement et al. ................. 606/61 |
| 2009/0270916 A1* | 10/2009 | Ramsay et al. ............... 606/246 |
| 2010/0168796 A1* | 7/2010 | Eliasen et al. ................ 606/264 |

* cited by examiner

*Primary Examiner* — Jerry Cumberledge
*Assistant Examiner* — Nicholas Plionis
(74) *Attorney, Agent, or Firm* — D'Ambrosio & Menon, PLLC; Usha Menon (57) ABSTRACT

Apparatus for use in stabilizing and/or aligning the spinal column utilizes hooks and rods to effectively transfer load from the vertebrae to the apparatus regardless of the angle and the height of the pedicular screws. A screw cap formed of a base having a bore therethrough for receiving the head of the screw, an upright riser formed thereon that is laterally offset from the bore, and a surface for engaging the rod or plate of the stabilizer enables the apparatus to be used for stabilizing and/or aligning vertebral bodies that are out of alignment, of different shape or size, and/or pathology. The apparatus is implanted in a series of steps that are quickly and conveniently performed in the surgical stage and with minimal application of force to align the vertebral bodies, decreasing the likelihood of damaging the nerves populating the surgical stage.

12 Claims, 9 Drawing Sheets

ROD AND PLATE SYSTEM FOR INCREMENTAL REDUCTION OF THE SPINE

CROSS-REFERENCE TO RELATED APPLICATION

This application in a continuation-in-part of application Ser. No. 12/148,006, filed Apr. 15, 2008, now abandoned entitled APPARATUS AND METHOD FOR ALIGNING AND/OR STABILIZING THE SPINE, the disclosure of which is hereby incorporated into this specification in its entirety by this specific reference.

BACKGROUND OF THE INVENTION

The present invention relates to alignment and/or stabilizing of the spinal vertebrae. More specifically, the present invention relates to a polyaxial spinal stabilizer and/or alignment system that effectively transfers the load from the vertebrae to the stabilizer using structure that facilitates surgical implantation of the system.

Stabilization and/or alignment of the spinal column is indicated for treatment of many pathologies including trauma, tumor, infection, degenerative spine disease, congenital, iatrogenic spinal instability, spondylolysis/spondylolisthesis, pseudarthrosis, kyphosis, scoliosis, and/or other spinal deformity. A number of stabilizers for treating such pathologies that utilize "hook and rod" components are disclosed in the scientific and patent literature and are available from such vendors as Sofamor-Danek, Osteonics, and others. Such stabilizers utilize screws that are driven into the bodies of adjacent vertebrae, typically in the pedicular region of the vertebral body, and rods that are secured to two, three, or more screws on adjacent segments using hooks that are either formed on or attached to the heads of the screws to stabilize and/or align the vertebrae.

A problem that arises during surgical implantation of such systems involves attachment of the screw to the rod. Depending upon the location on the spine, size of the vertebrae, pathology, and other factors unique to the patient, the screw heads extend at different angles and heights relative to the longitudinal axis of the spine even on adjacent vertebrae. For this reason, it can be difficult for the surgeon to attach the rod or plate to the screws, particularly when the patient suffers from spinal deformity. When a hook and rod system is used to stabilize the spine, the rod can be bent before it is attached to the screw, but when utilized to correct spinal deformity, the rod must be brought to the screw heads such that the connection between the screws and the rod must sometimes be accomplished using brute force. Of course the plate of a plating system cannot be formed or bent to align to the screws with the result that plating systems cannot be used in certain patients and/or for treatment of certain pathologies. In the case of a rod system in which the rod is approximated to the screw heads, the surgeon is working in a surgical stage populated with nerves and other tissues to which the application of force is anathemic. For these and other reasons, there is a need for improvement in such instrumentation, and it is an object of the present invention to provide such improvements.

Another object of the present invention is to provide an apparatus for use in aligning and/or stabilizing the spinal column that reduces the likelihood of traumatic injury to the spinal cord during surgery.

Similarly, in large part because of the difficult geometry caused by the different angles and heights of the pedicular screws, the transfer of the load that is normally carried by the spinal column to the stabilizer through the connection between rod and screw is problematical. Not only must this connection effectively transfer load from vertebrae to spinal stabilizer, but the transfer must be accomplished at any of a plurality of angles between pedicular screws and stabilizer. Several prior art devices appear to address this problem, an example being the pedicular screw and hook believed to be marketed under the trademark ISOBAR by Scient'x (Maitland, Fla., www.scientxusa.com). However, the structure of this prior art device does not facilitate attachment of the rod to the hook when pedicular screws do not line up and/or extend to different heights. It is therefore also an object of the present invention to provide an apparatus and method for effectively transferring load from the spinal column to a spinal stabilizer regardless of the angle and height of the heads of the pedicular screws that anchor the stabilizer to the patient's spine.

It is also an object of the present invention to provide an apparatus and method that facilitates attachment of a rod or plate to a spinal stabilizer by enabling the rod or plate of the spinal stabilizer to be incrementally advanced, or re-positioned, until the rod or plate is positioned so as to allow attachment to the pedicular screws with minimal danger to the nerves and other sensitive tissues within the surgical stage.

There is also a need for instrumentation for use in surgical treatment of spinal deformity and pathology that, because of the ability to incrementally advance the rod or plate to the screw head and to securely lock the rod or plate to the screw head, can be used to conform the rod or plate to the individual patient and to the geometry and configuration of the patient's anatomy, and it is an object of the present invention to provide apparatus and methods meeting that need.

There is also a need for instrumentation that is adaptable for use with both a hook and rod spinal stabilizer and a plating system as needed for stabilization of the patient and/or for alignment of the spine.

There is also a need for instrumentation for use in surgical treatment of spinal deformity and pathology that minimizes surgical trauma and it is also an object of the present invention to provide apparatus and methods meeting that need.

Another object of the present invention to provide instrumentation for use in aligning the spinal column having a construction that reduces the so-called "fiddle factor" involved in the surgery, shortening the duration of the surgical procedure.

It is also an object of the present invention to provide an apparatus in which the rod or plate of a spinal stabilizer is locked against movement relative to the pedicle screw regardless of the angle between the rod or plate and the screw.

It is also an object of the present invention to provide a washer for a spinal stabilizer, particularly a spinal stabilizer that comprises a rod, that is capable of providing a secure connection between the rod and a pedicle screw to which the washer is mounted at any angle relative to the rod.

Another object of the present invention is to provide a cap for receiving a pedicular screw and either the rod or the plate of a spinal stabilizer or alignment device comprising a base having (1) a bore therethrough for receiving the head of the pedicular screw, (2) a threaded post or riser, the bore and the post being offset from each other, and (3) a surface formed thereon adapted for engaging either the rod or the plate of the spinal stabilizer, relative movement of the pedicular screw, base, and the rod or plate being resisted when a nut is tightened on the threaded post.

Other objects, and the many advantages of the present invention; will be made clear to those skilled in the art in the following detailed description of several preferred embodiments of the present invention and the drawings appended hereto. Those skilled in the art will recognize, however, that the embodiments of the invention described herein are only examples provided for the purpose of describing the making and using of the present invention and that they are not the only embodiments of spinal stabilizers that are constructed in accordance with the teachings of the present invention.

SUMMARY OF THE INVENTION

The present invention provides solutions for the above-described problems by providing a screw cap for use in a system for aligning and/or stabilizing the spinal column comprising a pedicle screw, a threaded nut, and either a rod or a plate. The screw cap comprises a base having a bore therethrough for receiving the head of a pedicle screw and a riser formed thereon for receiving a threaded nut, the axis of the riser and the axis of the bore in the base being laterally offset from each other, and a washer having a bore therethrough for receiving the riser formed on the base and a surface adapted for engagement by either a rod or a plate, movement of the rod or plate relative to the base being resisted when a nut received on the riser is tightened.

The present invention also provides a washer that is adapted for use with an apparatus for incrementally aligning the spinal column comprising a pedicle screw and either a rod or a plate, the pedicle screw having a head either with (a) threads formed thereon for receiving a nut for tightening the rod or plate to the head of the pedicle screw or (b) structure formed thereon for receiving a screw cap having threads formed thereon for receiving a nut for tightening the rod or plate to the head of the pedicle screw. The washer comprises a surface adapted for engaging either the head of the screw or the screw cap, or both the head of the screw and the screw cap. A concave surface is formed on the washer for engaging the rod or plate and the washer further comprises a surface adapted for engagement by a nut either received on the threads formed on the head of the pedicle screw or the threads formed on the screw cap.

In another aspect, the present invention provides a washer formed in the shape of a right, substantially circular cylinder and having a bore therethrough. The axis of the bore is substantially parallel to the axis of the cylinder, and the washer is further provided with an elongate groove, the axis of the groove being substantially perpendicular to the axis of the cylinder, and the opening of the groove forming a mouth in the surface on one end of the cylinder. In a particularly useful embodiment, the groove formed in the washer is substantially cylindrical and the concave surface forming the groove defines a surface forming an arc that extends more than 180° such that the groove forms a mouth, or narrowed opening, in the surface of the washer and the diameter of the cylindrical groove is slightly larger in dimension than the dimension of the mouth of the groove so that the washer can be snapped onto a retained on the rod. In a preferred embodiment, a plurality of washers are snapped onto a rod before the rod is introduced into the surgical stage and are moved lengthwise along the length and rotated around the rod to facilitate matching the washers up with the heads of pedicle screws that have already been affixed to the vertebral bodies of the patient.

In yet another aspect, the present invention provides a method of incrementally aligning the spine comprising the steps of:

affixing a pedicle screw to adjacent vertebral bodies at selected angles and heights relative to the vertebral body, each pedicle screw having the base of a screw cap retained thereon, the base of the screw cap being provided with a threaded post;

placing a washer comprising the screw cap over each respective threaded post;

capturing either a rod or a plate that extends along the longitudinal axis of the spine between the washer and the screw cap base, surfaces being formed on both the washer and the screw cap base for engaging the rod; and tightening a nut on the threads of the screw cap base to incrementally advance the vertebral body to which the pedicle screw is affixed toward the rod or plate.

The method of the present invention also contemplates resisting relative movement between the pedicle screw and the base of the screw cap.

BRIEF DESCRIPTION OF THE DRAWINGS

Referring now to the figures.

DETAILED DESCRIPTION OF THE PREFERRED EMBODIMENT(S)

Figure 1:
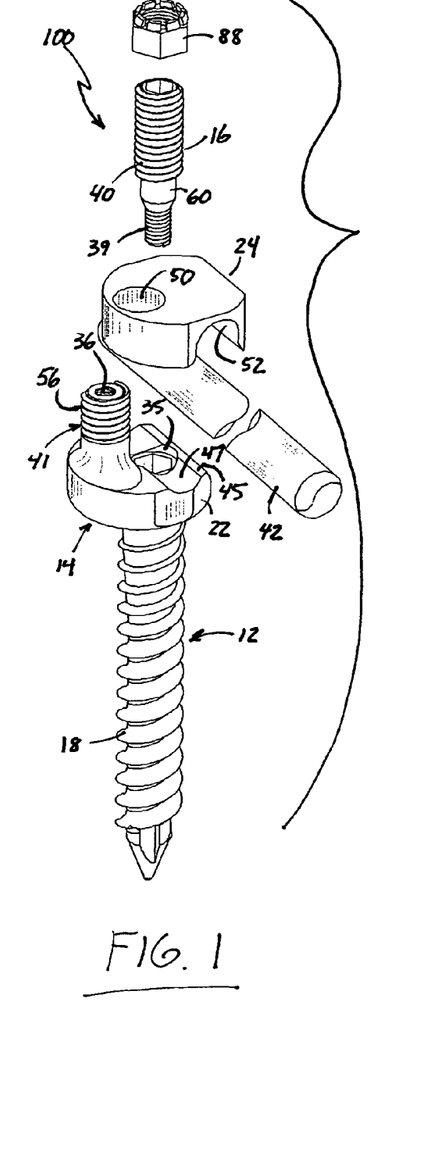
FIG. 1 shows an exploded, perspective view of a first embodiment of an apparatus for use in aligning and/or stabilizing the spinal column constructed in accordance with the teachings of the present invention.

In more detail, FIGS. 1-3 show a first embodiment of an apparatus, indicated generally at reference numeral 10, for aligning and/or stabilizing the spinal column constructed in accordance with the present invention. Apparatus 10 is comprised of pedicle screw 12 and screw cap 14, screw 12 being of a type known in the art comprised of an elongate threaded shank 18 and head 20. Screw cap 14 is comprised of base 22 and washer 24, with means 26 formed in base 22 for retaining screw cap 14 to the head 20 of screw 12. As shown in FIGS. 3C and 3D, screw cap retaining means 26 takes the form of a cavity 28 formed in the base 22 of screw cap 14, cavity 28 being sized so as to receive the rounded head 20 of screw 12 therein while allowing screw cap 14 to be positioned in an unlimited number of positions relative to screw 12 during surgical fixation to the patient's vertebral body such that the cavity 28 and the head 20 of screw 12 function in a manner similar to a ball and socket joint. The ability to position screw cap 14 at an unlimited number of positions relative to screw 12 facilitates attachment of the rod of an external spinal stabilizer and/or apparatus for alignment of the spine to the screw 12 in the manner described below. In the embodiment shown, screw cap retaining means 26 comprises a screw thread 27 formed on the outside surface of the head 20 of screw 12 and a complimentary thread 29 formed on the inside surface of the opening 30 into the cavity 28 in the base 22 of screw cap 14. This structure of screw cap retaining means 26 allows the head 20 of screw 12 to be drawn into cavity 28 by rotating screw cap 14 relative to screw 12 (so that threads 27, 29 engage each other) and then retained in cavity 28 while the narrow neck 32 formed in screw 12 allows the screw cap 14 to be oriented at an unlimited number of positions relative to the long axis of screw 12 (in other words, the axis of the shank 18 of screw 12 and the axis of the opening 30 into the cavity 28 of screw cap 14 need not be aligned on a common axis, or coincident, as shown schematically in FIG. 2) to facilitate the connection between a rod and the screw 12 regardless of the angle between the long axis of screw 12 and the longitudinal axis of the spinal column, as well as the longitudinal axis of a rod such as the rod 42 shown in FIG. 1 or plate such as shown in FIG. 7. Because screw cap retaining means 26 allows the screw cap 14 to be oriented at an unlimited number of positions, or angles, relative to the long axis of screw 12, the connection between rod 42 and screw 12 through screw cap 14 is referred to as being "polyaxial."

Figure 2A:
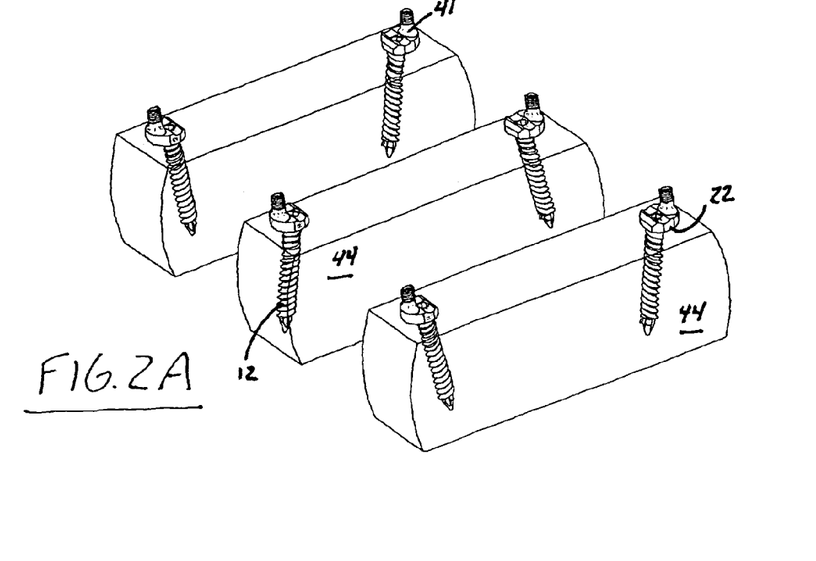
FIG. 2 is a series of partially schematic, perspective views (labeled as FIGS. 2A-2F) of three vertebral bodies of the spinal column, FIGS. 2A-2E showing the steps of implanting the apparatus of FIG. 1 in a patient and FIG. 2F showing the manner in which a the rod comprising one of the component parts of the apparatus of FIG. 1 is bent for use of the apparatus of FIG. 1 for incremental alignment of the spine.
Figure 2B:
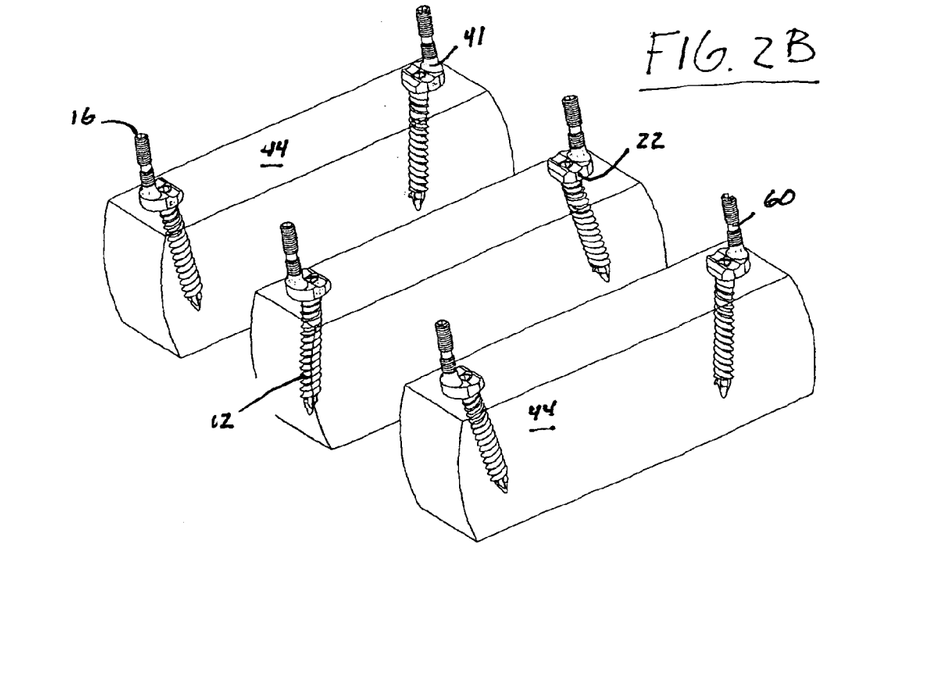
Figure 2C:
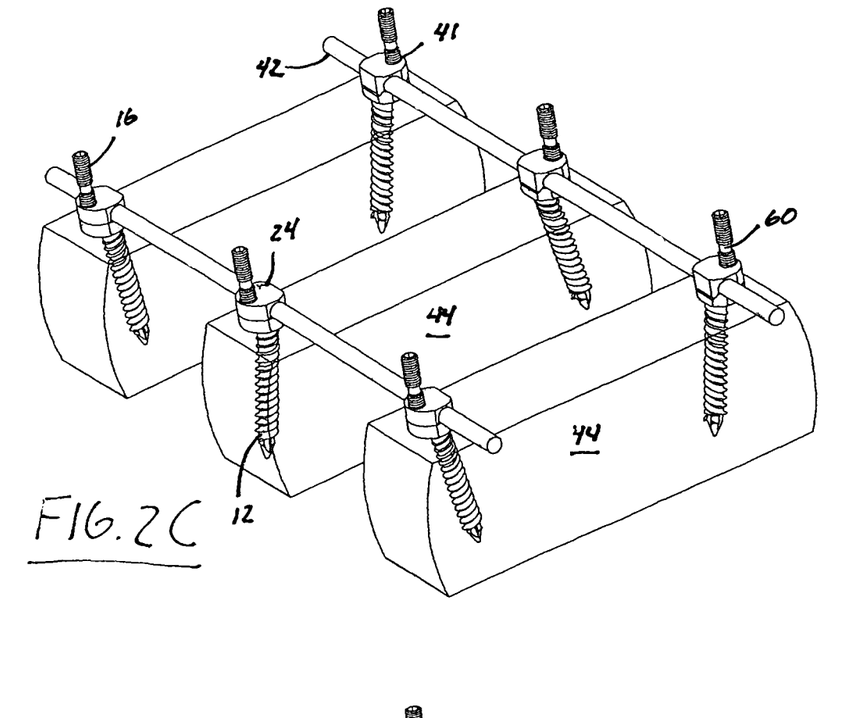
Figure 2D:
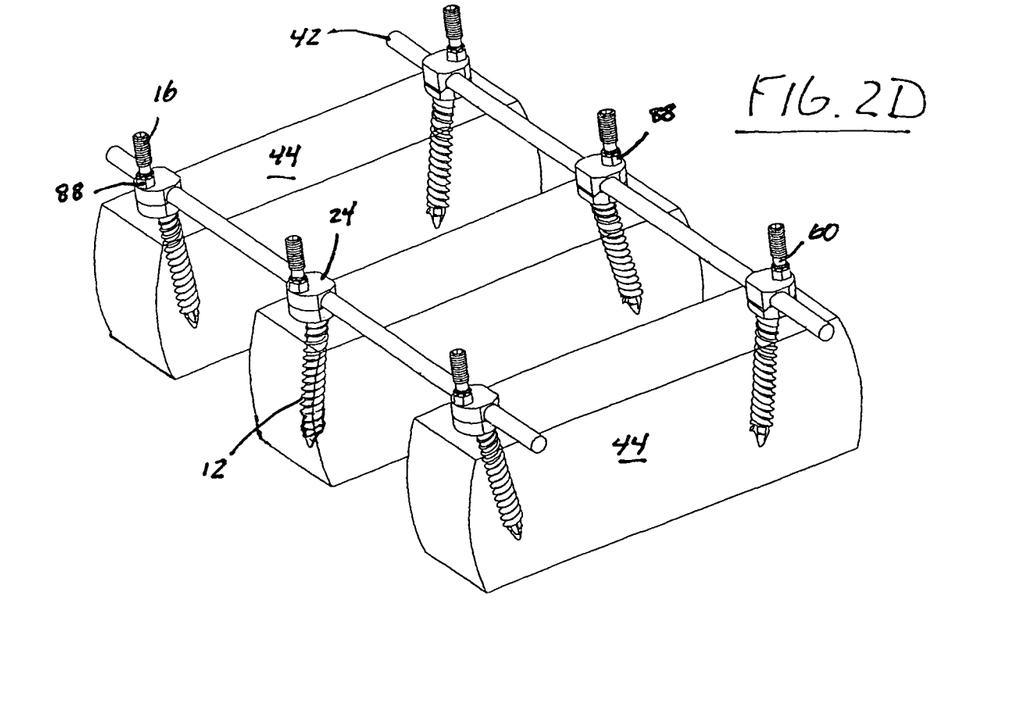
Figures 2E, 7:
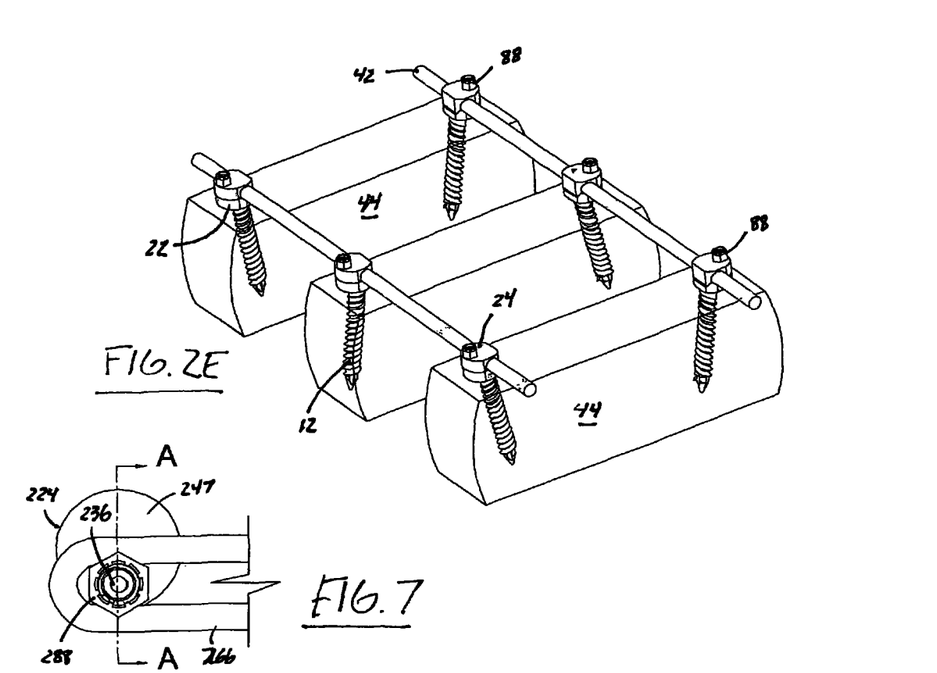
FIG. 7 is a top, plan view of another alternative embodiment of an apparatus for use in aligning and/or stabilizing the spinal column that is constructed in accordance with the teachings of the present invention.
Figure 2F:
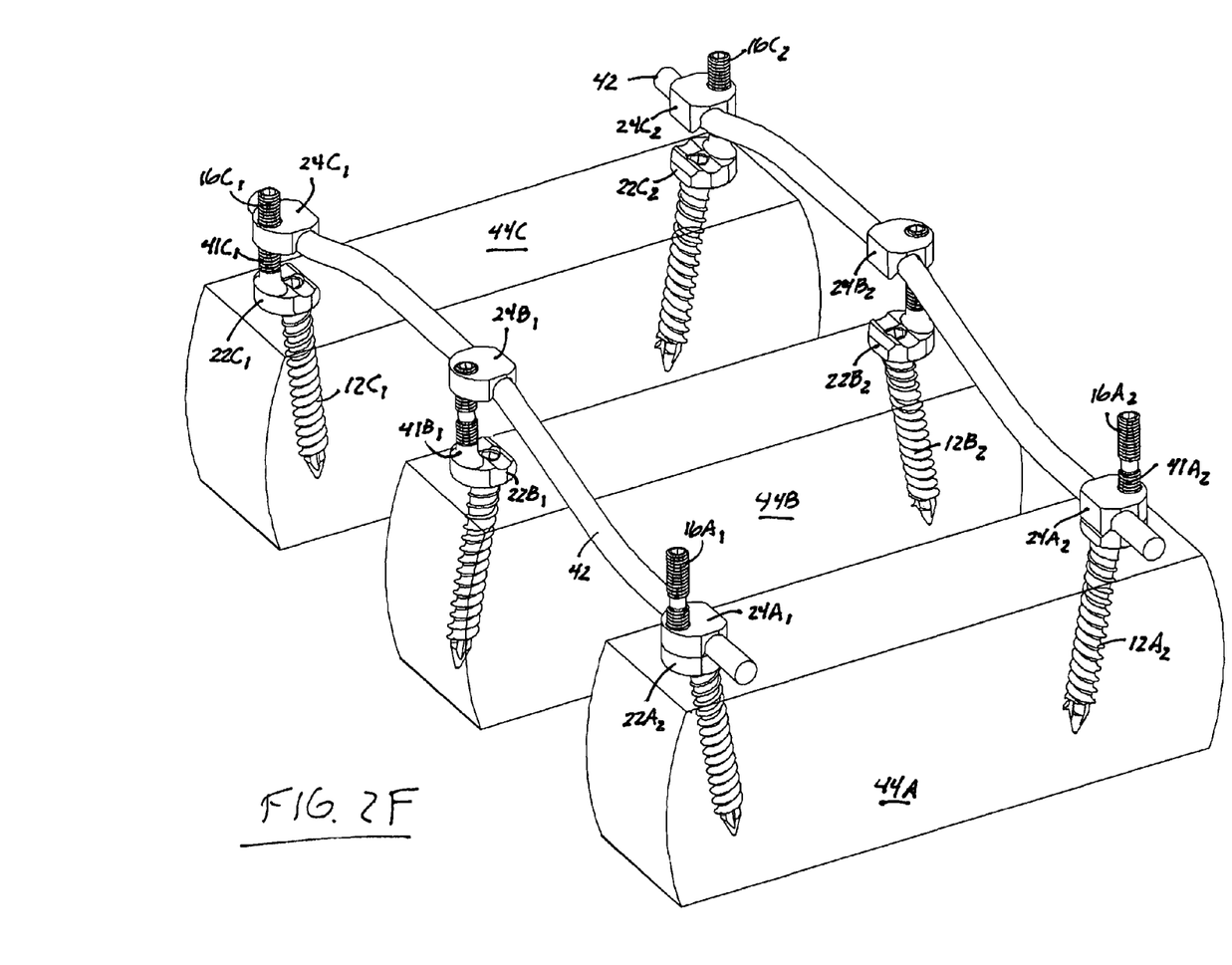
Figure 3A:
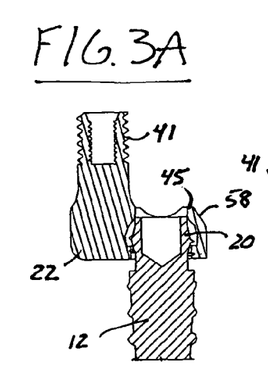
FIG. 3 is a series of sectional views (labeled as FIGS. 3A-3E, corresponding to FIGS. 2A-2E) of the apparatus of FIG. 1 at each of the steps of implantation in a patient.
Figures 3B, 3E:
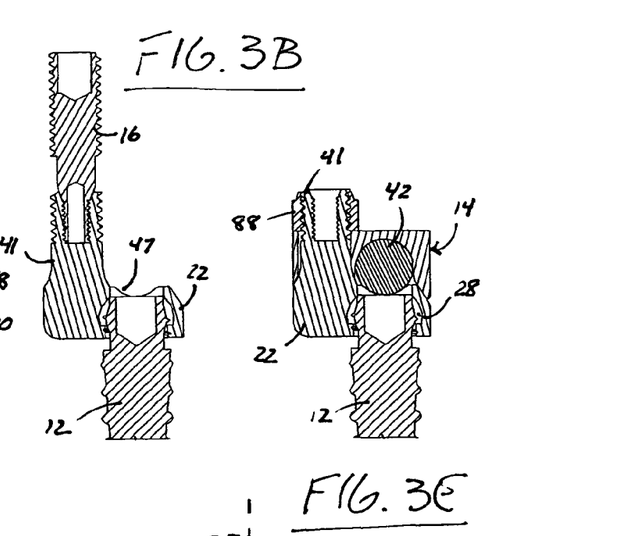
Figure 3C:
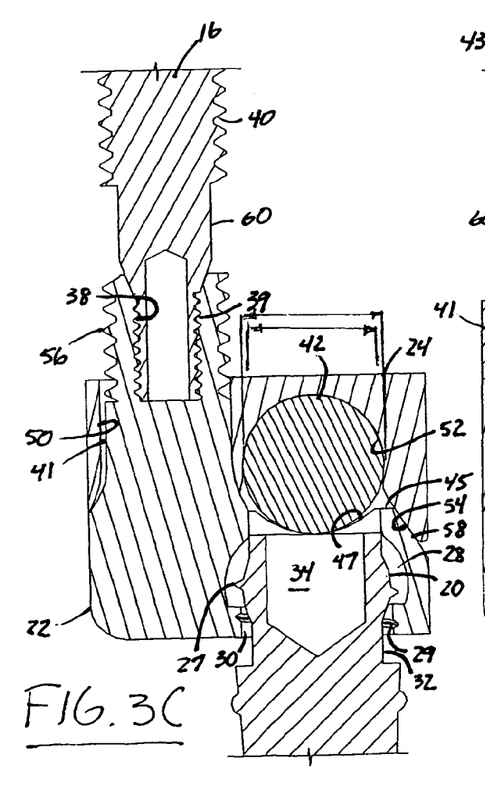
Figure 3D:
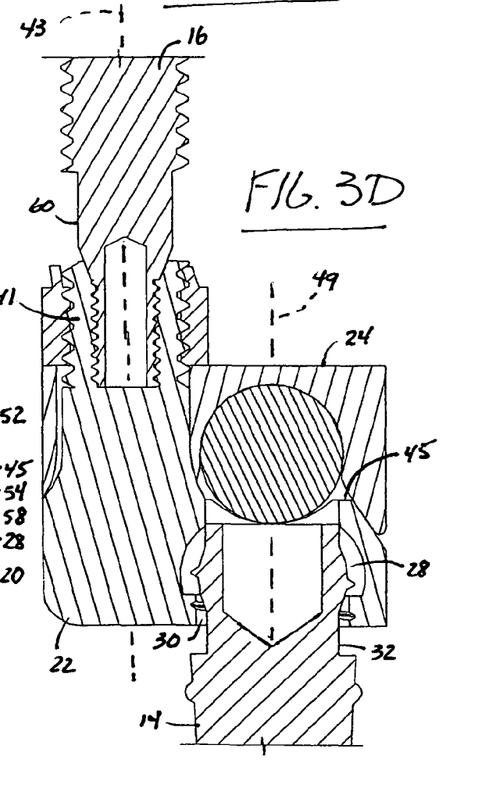

As best shown in FIGS. 3C and 3D, the head 20 of screw 12 is provided with a bore 34 for receiving an instrument (not shown) for rotating screw 12 to drive screw 12 into vertebral body 44 (the latter being shown schematically in FIG. 2). In the embodiment shown, bore 34 is shaped to receive a complimentary-sized hex key (not shown) for rotating screw 12. Similarly, the upright, threaded riser 41 formed on screw cap 14 is provided with a bore 36 having threads 38 formed in the walls thereof for threadably receiving a threaded post 39 formed on an extension 16, thereby releasably securing extension 16 to screw cap 14 for a purpose described below. As shown in FIG. 3D, the longitudinal axis (indicated by shadow line 43) of the upright riser 41 is laterally offset from the central axis (indicated by shadow line 49) of the opening 30 of cavity 28 for a purpose made clear below, and riser 41 is also provided with external threads 56 for receiving a lock nut 88 as described in more detail below for holding rod 42 in the cradle formed by the concave surface 47 of screw cap 14 to lock the rod 42 to the base 22 of screw cap 14. By reference to FIGS. 3C and 3D, it can be seen that the head 20 of screw 12 projects through the opening 35 of cavity 28 (opening 35 is shown with its reference numeral in FIG. 1) to a level slightly higher than the lowest point of concave surface 47 so that rod 42 pushes against the head 20 of screw 12 (which projects out of the top of cavity 28) so as to lock the screw 12 at a particular angle (or at least resist relative motion) relative to screw cap 14 and rod 42.

In addition to screw cap retaining means 26 and the concave surface 47 that is adapted for receiving and retaining a rod 42 to the screw cap 14, the base 22 of screw cap 14 comprises a raised portion, or lip 45. The riser 41 and lip 45 of base 22 together define a cradle formed in a concave shape that is closed by washer 24, washer 24 also being provided with a concave surface 52. The radius of the concave surface 52 formed in washer 24 approximates the outside diameter of rod 42 for receiving rod 42 therein when washer 24 is received on the upright riser 41 of screw cap 14. Washer 24 is formed in the shape of a right cylindrical cylinder and is provided with a bore 50 sized so as to allow the washer to drop down over riser 41 and onto the base 22 of screw cap 14 (note that bore 50 is not threaded and therefore capable of moving in an unrestricted manner up and down on the outside diameter of riser 41). Although washer 24 is shown and described as being formed as a right circular cylinder, those skilled in the art who have the benefit of this disclosure will recognize that an exact right circular cylinder is not required and that there may even be cause for the washer 24 not to be an exact right circular cylinder and/or for the ends of the cylindrically-shaped washer not to be parallel depending upon the particular geometry and/or pathology presented by the needs of the patient. For this reason, the washer is referred to herein as being shaped as a right, substantially circular cylinder. A bevel 54 is formed on washer 24 that is received on, or registers with, a complimentary-shaped surface 58 formed on the base 22 of screw cap 14. As is apparent from FIG. 3D, when lock nut 88 is tightened down against the top surface (not numbered) of washer 24 on the threads formed on upright riser 41, the concave surface 52 formed on the underside of washer 24 bears against rod 42 to lock rod 42 against motion relative to screw cap 14 and to resist relative motion between rod 42 and screw 12 because the outside diameter of rod 42 is forced against the top of the head 20 of screw 12 projecting through the opening 35 of the cavity 28 formed in the base 22 of screw cap 14 and the surface 47 functions as a bearing surface for the surface of rod 42.

In one embodiment that facilitates the surgical implantation of the rod system of the present invention, the concave surface 52 formed in the underside of each washer 24 defines an arc that extends slightly more than 180° around the external surface of rod 42 forming a mouth, or narrowed opening, 53 in the surface of the underside of washer 24 that enables the hooks 24 to be snapped onto the rod 42 by exerting pressure on the top surface of each washer 24. This opening 53 is shown by the dimensional lines D and R in FIGS. 1 and 3C, the dimensional line D (FIGS. 1 and 3C) representing the diameter of rod 42 and the line R (FIG. 3C), which is slightly shorter than the line D, representing the dimension, or width, of the opening 53 of concave surface 52 on the underside of washer 24. By snapping the rod 42 through opening 53, the washers 24 are retained on rod 42 but still capable of sliding along the length of the rod 42 and rotating around rod 42 to facilitate positioning of the washers 24 at irregular intervals and different angles so that washers 24 can be quickly and easily dropped down onto the tops of the bases 22 of screw caps 14 that are already in place on the patient's vertebral bodies 44 by fitting the risers 41 (or extensions 16) through the bores 50 formed in each of washers 24.

Referring now to FIGS. 2A-2E and 3A-3E, the steps of a presently preferred embodiment of a method for implanting the apparatus 10 will now be described. After pedicular screws 12 of the length and diameter appropriate for the patient have been selected, the screw cap 14 is assembled to the head 20 of screw 12 by engaging the thread 27 formed on the outside diameter of head 20 to the complimentary thread 29 formed in the inside diameter of the opening 30 of the cavity 28 in the base 22 of screw cap 14 and rotating screw cap 14 relative to screw 12 until the head 20 of screw 12 is drawn into the cavity 28, where it is retained by the narrow opening 30, which is sized to fit closely around the neck 32 of screw 12. Because the screw cap 14 and screw 12 are not rotated relative to one another once implanted, the likelihood of engagement of the threads 27, 29 in a way that would allow the head 20 to back out of the cavity 28 is next to zero, and once positioned in the cavity 28 of screw cap 14, the threads 27 do not engage the inside diameter of cavity 28 such that the screw 12 is free to move relative to screw cap 14 so that screw 12 can be positioned at any of a plurality of angles relative to screw cap 14 as screw 12 is driven into the vertebral body 44. The assembly comprised of screw 12 and screw cap 14 is then driven into a vertebral body 44 using a hex key (not shown) that engages the bore 34 in the head 20 of screw 12 as described above, FIG. 2A showing pedicular screws 12 that have been driven into three adjacent segments. Note that the shanks 18 of the screws 12 shown in FIG. 2A are oriented at different angles relative to the screw caps 14 as required by such factors as the shape and size of the vertebral bodies and the particular pathology of the patient.

As shown in FIG. 2B, the threaded extensions 16 are then mounted to screw caps 14 by engagement of the threaded post 39 of each extension 16 to the internal threads 38 in the bore 36 of the respective risers 41 on the base of each screw cap 14. Although they are shown in FIG. 2 as being more or less aligned on the longitudinal axis of the spinal column of the patient, it will be appreciated by those skilled in the art that the vertebral bodies of some patients may not be spaced at regular intervals or aligned on the longitudinal axis of the spinal column, and are therefore in need of alignment. The extensions 16 on each screw cap 14 provide threads 40 that extend in the dorsal direction to sufficient height that the apparatus of the present invention can be utilized for aligning and/or stabilizing the vertebral bodies of the abnormal and/or pathological spinal column.

In the next step, shown in FIG. 2C, a plurality of washers 24 are assembled to rod 42 in the manner described above and each washer 24 is then assembled to the base 22 of its respective screw cap 14 in the surgical stage. As described above, the washers 24 are snapped onto the rod 42 by exerting pressure on the top surface of each washer 24 but can be moved along the length of the rod 42 and rotated around rod 42 to facilitate the positioning of the washers 24 so that the extensions 16 (or risers 41) that are already in place on the patient's vertebral bodies 44 can be inserted through the bores 50 of the respective washers 24.

However, it will be apparent to those skilled in the art that because of the pathology of the patient and the variability in size, shape, and position of the vertebral bodies, the washers 24 may not drop all the way down over the extensions 16 and upright risers 41 of screw caps 14. By threading the lock nut 88 onto the threads 40 of extensions 16 and rotating the lock nut 88 until it engages the top surface of each respective washer 24, and then continuing to rotate the lock nut 88 so as to force the rod 42 toward the respective base 22 of screw cap 14, rod 42 functions to incrementally move the vertebral body 44 toward the rod 42 with the result that adjacent vertebral bodies are brought closer into alignment with rod 42 regardless of the orientation of the pedicular screws 12 relative to rod 42 and screw cap 14. To facilitate tightening the nut 88 against the washer 24 of screw hook 14, extension 16 is provided with an unthreaded portion, or refresher gap, 60 located at the end of extension 16 proximate threaded post 39. The dimension of refresher gap 60 is slightly larger than the height of the lock nut 88 so that after nut 88 has been advanced down the threads 40 of extension 16, pushing rod 42 toward the cradle formed by the surface 47 on screw cap 14, nut 88 turns freely around the unthreaded gap 60 of extension 16, thereby facilitating engagement of the threads 56 on the upright riser 41 of screw cap 14 by nut 88. By further tightening of nut 88 on the threads 56, the bevel 54 on washer 24 engages the complimentary surface 58 of screw cap 14 to approximate the washer 24 with the respective base 22 so that rod 42 is forced into engagement with the surfaces 47 and 52 formed on the base 22 and washer 24, respectively, of screw cap 14. Further rotation of nut 88 tightens the hook against rod 42 with the result that rod 42 is forced against the head 20 of screw 12, which projects through the opening 35 in surface 47 in the manner described above, to lock screw 12 against movement relative to screw cap 14 and rod 42. Referring to FIG. 2E, it can be seen that the extensions 16 are then removed from the screw caps 14 by rotating out of the bore 36 on threads 38.

As noted in several previous paragraphs, the ability of the surgeon to use the rod system of the present invention to incrementally align the spine is of particular importance. As also noted above, the rod of a hook and rod system is bent by the surgeon before it is attached to the pedicular screws so that the screw heads (after the screws have, of course, already been driven into the vertebral bodies) are moved to the rod to align the screws and the vertebral bodies to which they are affixed. The use of the rod system of the present invention in this manner is further illustrated in FIG. 2F, which shows a stage in the method described in the previous paragraph that is approximately intermediate the stages shown in FIGS. 2C and 2D. As shown in FIG. 2F, each of the rods 42 has been bent, or formed, by the surgeon as needed and the washers $24A_1$ and $24A_2$ have been fitted over the extensions $16A_1$ and $16A_2$ so that the ends of each of rods 42 have been effectively sandwiched between the washers $24A_1$ and $24A_2$ and bases $22A_1$ and $22A_2$ of screw caps $14A_1$ and $14A_2$ so that respective nuts 88 can be tightened against the washers $24A_1$ and $24A_2$ to fix the rods 42 and screw caps $14A_1$ and $14A_2$ in place relative to each other. Despite the bending of the rods 42 as shown, the different heights of the extensions affixed to the screw caps at each of the three levels of the spine, resulting from misalignment or pathology of the vertebrae, are apparent by comparison of the locations of the washers $24B_1$ and $24B_2$ along the threads 40 of extensions $16B_1$ and $16B_2$ and the washers $24C_1$ and $24C_2$ along the threads 40 extensions $16C_1$ and $16C_2$. By threading nuts 88 onto the respective extensions 16B and 16C and then tightening nuts 88, the vertebral body 44B is incrementally drawn toward the rods 42 by snugging the respective bases $22B_1$ and $22B_2$ of screw hooks $14B_1$ and $14B_2$ up against the respective washers $24B_1$ and $24B_2$ located on the rods 42 and are therefore initially spaced apart from the surface of the vertebral body 44B, rather than by snugging the washers $24A_1$ and $24A_2$ downwardly into engagement with the bases $22A_1$ and $22A_2$ as was the case for screw hooks $14A_1$ and $14A_2$. To a lesser extent, the vertebral body 44C is drawn toward the rods 42 in the same manner by tightening the nuts threaded onto the extension $16C_1$ and $16C_2$ of each of the screw hooks $14C_1$ and $14C_2$. Of course nuts 88 are threaded onto the extensions $16A_1$ and $16A_2$ affixed to the bases $22A_1$ and $22A_2$ of screw caps $14A_1$ and $14A_2$ to complete the process. The result of the incremental movement of the vertebral bodies 44B and 44C caused by tightening the nuts 88 at each level of the spine is that the vertebral bodies are aligned in the manner planned by the surgeon with minimal danger to the nerves and sensitive tissues in the surgical stage and with minimal trauma, while at the same time providing precise control of the movement of the vertebral bodies such as cannot generally be attained by the use of methods that require exertion of brute force.

Figure 4:
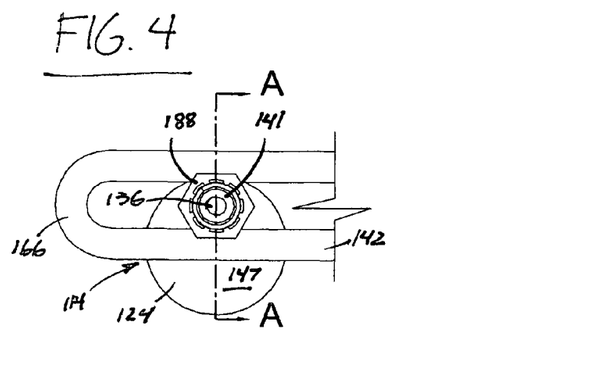
FIG. 4 is a top, plan view of an alternative embodiment of an apparatus for use in aligning and/or stabilizing the spinal column that is constructed in accordance with the teachings of the present invention and in which the rod of the embodiment shown in FIGS. 1-3 is replaced by a plate.
Figures 5A, 5B, 5C, 11:
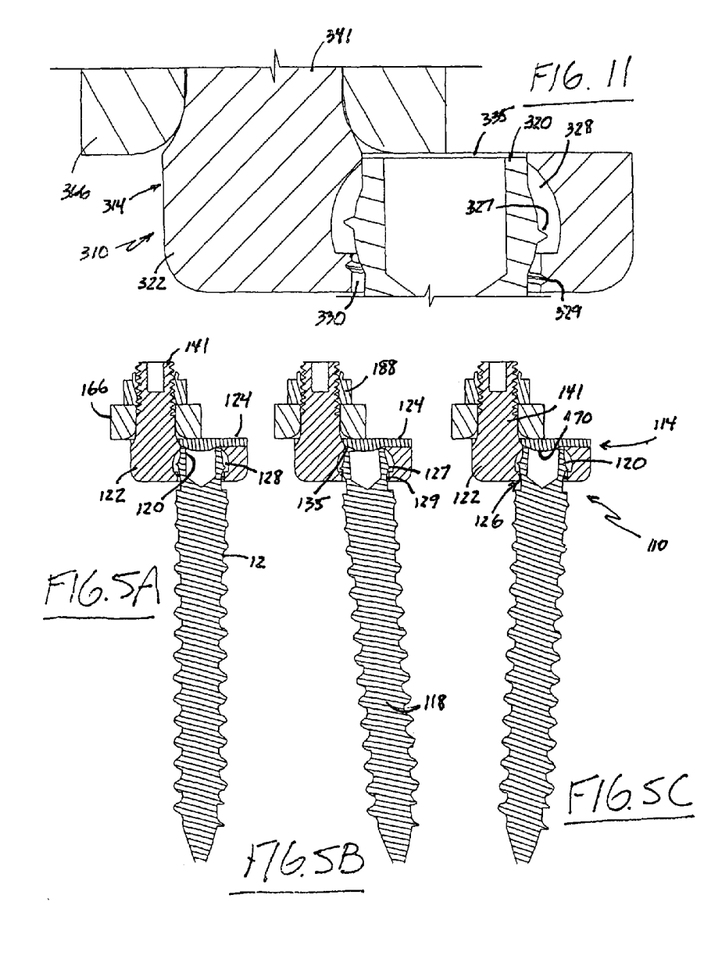
FIGS. 5A, 5B, and 5C are a series of sectional views of the apparatus shown in FIG. 4, FIG. 5A being a sectional view taken along the line A-A in FIG. 4 and FIGS. 5B-5C being similar sectional views, showing that a pedicle screw can be oriented at different angles relative to the screw cap comprising the apparatus shown in FIG. 4 for affixation to the vertebral body.
FIG. 11 is an enlarged sectional view of yet another alternative embodiment of an apparatus for use in aligning and/or stabilizing the spinal column that is constructed in accordance with the teachings of the present invention.
Figures 6A, 6B:
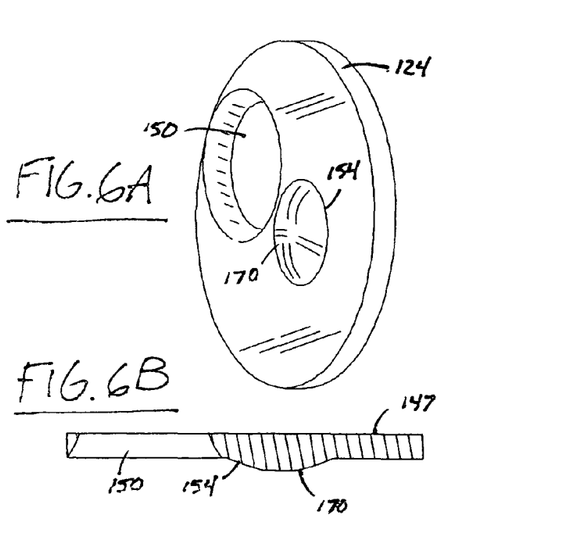
FIGS. 6A and 6B are perspective and sectional views, respectively, of a washer that forms a portion of the screw cap of the apparatus shown in FIGS. 4 and 5.

In a second embodiment shown in FIGS. 4-6 in which reference numerals corresponding to the reference numerals of the component parts shown in FIGS. 1-3 are designated by like reference numerals preceded by a "1," the apparatus is indicated generally at reference numeral 110. Screw cap 114 is comprised of base 122 and washer 124, base 124 being provided with a bore 128 extending therethrough and riser 141, and as best shown in FIG. 4, the longitudinal axis (not labeled in the figures) of riser 141 is laterally offset from the central axis (also not labeled) of bore 128 in the same manner as described above in connection with the embodiment shown in FIGS. 1-3. Washer 124 is formed in the shape of a right circular cylinder and is comprised of bore 150 (FIG. 6) through which riser 141 is received (see FIG. 5) and surface 147 adapted for engaging plate 166. Referring also to FIGS. 5 and 6, it can be seen that washer 124 is provided with a raised area 154 that drops into the opening 135 (best shown in FIG. 5B because of the angle at which the shank 118 of screw 112 is oriented relative to the central axis of the bore, or cavity, 128 in the base 122 of screw cap 114) of cavity 128 in base 122 and therefore functions to align washer 124 with base 124 when washer 124 nut 188 is tightened in much the same way that the beveled surface 54 of washer 24 cooperate as described above in connection with the embodiment shown in FIGS. 3C and 3D.

The apparatus 110 is further provided with means 126 for retaining the head 120 of screw 112 to the base 122 of screw cap 114 in the form of the external thread 127 on the head 120 of screw 112 and the thread, or lead-in groove, 129 cut in the inside wall of the opening 130 to the cavity 128 in the base 122 of screw cap 124 which function in the manner described above in connection with the embodiment shown in FIGS. 1-3. As shown in FIGS. 5A, 5B, and 5C, the raised area 154 of washer 124 projects downwardly into the opening 135 of the bore 128 through the base 122 of screw cap 114 when the nut 188 is tightened on riser 141, providing a surface 170 adapted for engaging the head 120 of the pedicle screw 112 residing in the bore 128. When the nut 188 is tightened against plate 166, washer 124 is trapped between plate 166 and the base 122 of screw cap 114 and the surface 170 bears against the head of screw 112 so as to lock, or at least resist, relative movement between the screw 112, screw cap 114, and plate 166. As is clear by comparison of FIGS. 5A, 5B, and 5C, relative movement between screw 112 and screw cap 114 is resisted regardless of the angle at which the shank 118 of screw 112 is positioned relative to the central axis of the cavity, or bore, 128 through the base 122 of screw cap 114, thereby allowing optimal placement of the screws 112.

Figure 8:
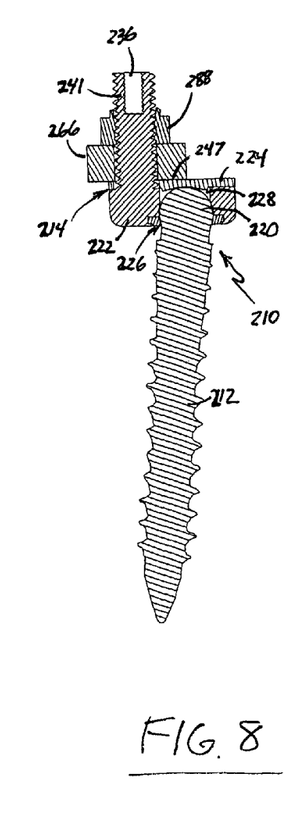
FIG. 8 is a sectional view of the apparatus of FIG. 8 taken along the line A-A in FIG. 8.
Figure 9A:
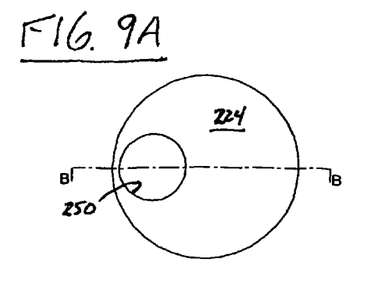
FIGS. 9A, 9B, and 9C are top, sectional, and perspective views, respectively, of a washer that forms a portion of the screw cap of the apparatus shown in FIGS. 7 and 8.
Figure 9B:
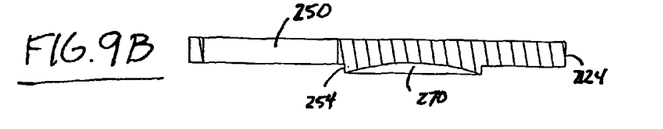
Figure 9C:
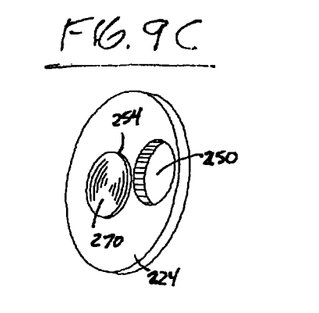

A third embodiment of the apparatus of the present invention is indicated generally at reference numeral 210 and shown in FIGS. 7-10 and the component parts of apparatus 210 are designated with the same reference numerals used for the corresponding parts of apparatus 10 shown in FIGS. 1-6, but preceded by a "2." Screw cap 214 is comprised of base 222 and washer 224, base 224 being provided with a bore 228 extending therethrough and an upright riser 241, and as best shown in FIG. 6, the longitudinal axis (not labeled) of riser 241 is laterally offset from the central axis (also not labeled) of bore 228 in the same manner as described above in connection with the embodiment shown in FIGS. 1-6. Washer 224 is comprised of a bore 250 through which riser 241 is received and a surface 247 adapted for engaging plate 266. Referring to FIGS. 8 and 9, it can be seen that washer 224 is provided with a raised area 254 that drops into the opening 235 of the cavity, or bore, 228 through the base 222 of screw cap 214 and therefore functions to align washer 224 with base 222 when nut 288 is tightened on riser 241 in much the same way that the beveled surface 54 of washer 24 cooperate as described above in connection with the embodiment shown in FIGS. 3C and 3D.

Means 226 is provided, in the form of a C-ring 268 positioned in the opening 230 to the bore 228 in base 222, for retaining the head 220 of screw 212 to screw cap 214. By reference to FIG. 7, it can be seen that the C-ring 268 cooperates with the curvature of the inside wall of bore 228 and the narrowed neck 232 of screw 212 to capture, or retain, the rounded head 220 of screw 212 while also allowing the shank 218 of screw 212 to be positioned at any of a plurality of angles relative to screw cap 214 and plate 266 (see FIGS. 10A-10D, noting the different angles of the shanks of screws 212 as required for proper placement in the vertebral bodies 244). C-ring 268 is retained in the base 222 of screw cap 214 by the complimentary shape of the walls of the opening 230 into bore 228. Although retaining means 226 includes a C-ring 268 and complimentary opening 230 as shown in FIGS. 7-10, it will be recognized by those skilled in the art that the retaining means 26 of the embodiment shown in FIGS. 1-3 is also utilized to advantage in the embodiment shown in FIGS. 7-10 (and of course the retaining means 226 could be substituted for retaining means 26 in the embodiment shown in FIGS. 1-6 and 11).

The raised area 254 of washer 224, which as described above, projects downwardly into the opening 235 of the bore 228 through the base 222 of screw cap 214 when the nut 288 is tightened on riser 241 is provided with a surface 270 adapted for engaging the head 220 of the pedicle screw 212 residing in the bore 228. When the nut 288 is tightened against the plate 266, the washer 224 is trapped between plate 266 and the base 222 of screw cap 214 and the surface 270 bears against the head of screw 212 so as to lock, or at least resist, relative movement between the screw 212, screw cap 214, and plate 266.

Figure 10A:
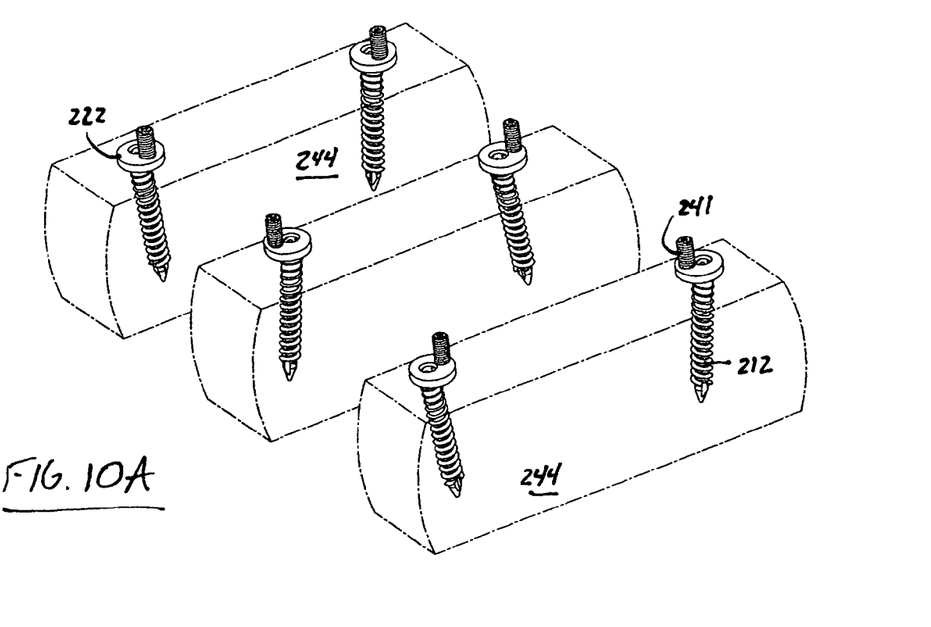
FIG. 10 is a series of partially schematic, perspective views (labeled as FIGS. 10A-10D) of three vertebral bodies of the spinal column showing the steps of implanting the apparatus of FIGS. 7-9 in a patient.
Figure 10B:
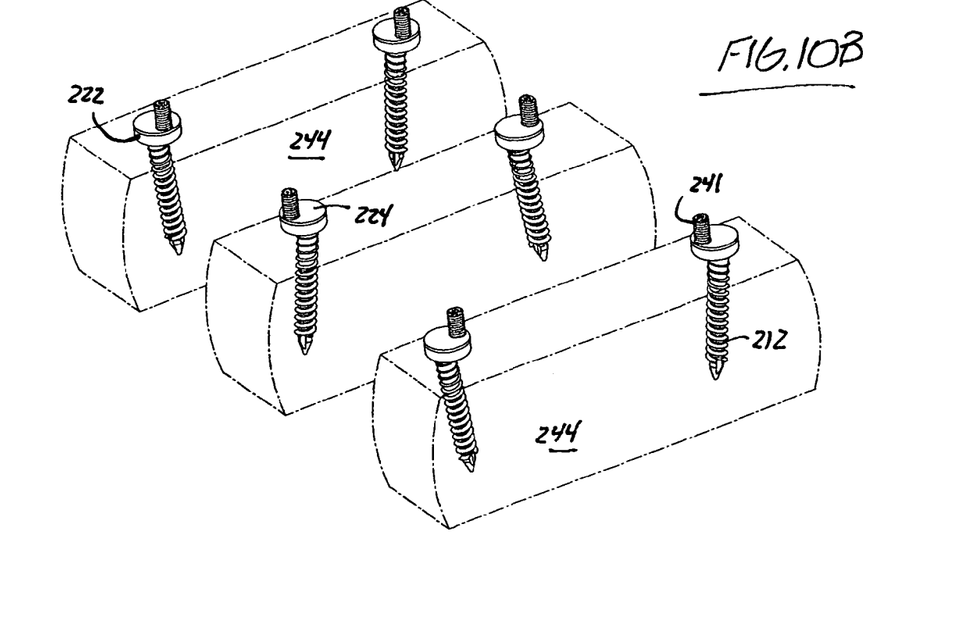

Referring now to FIGS. 10A-10D in addition to FIGS. 6-9, the steps in a preferred embodiment of the method of implanting the stabilizing apparatus 210 will be described in more detail. In the first step as shown in FIG. 10A, the pedicle screws 212, having the respective bases 222 of screw caps 214 retained thereon, are driven into the vertebral bodies 244 of the patient's spinal column. Note that the angles of the shanks 218 of the screws 212 may be different from one vertebral body 244 to the next because of the ability of the screws to be angled relative to the bases 222 of screw caps 214 as needed for proper placement of each screw and that, because of the offset risers 241 on each of the bases 222, the risers 241 are positioned at various degrees of rotation so as to best align the risers from one vertebral body 244 to the next as will be made clear in connection with the description of FIG. 10C, below. As shown in FIG. 10B, in the next step, of the method of the present invention, the washers 224 are assembled to the respective bases 222 of each screw cap 214 by dropping the washer 224 over the riser 241 of each base 224 and then positioning the washer 224 on the base 222 so that the raised surface 254 drops into the opening 235 of the bore 228 through the base 222, thereby aligning the washer 224 and base 222.

Figure 10C:
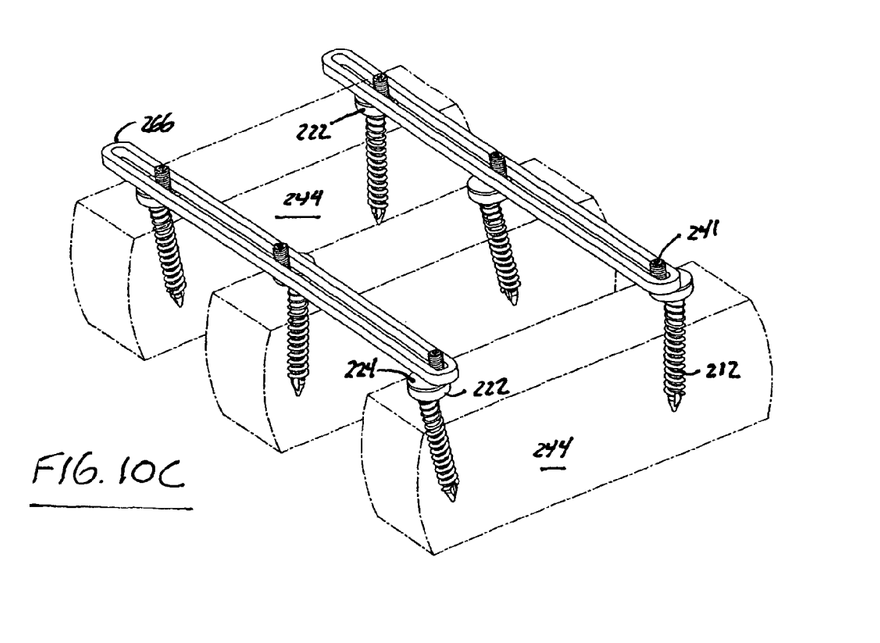
Figure 10D:
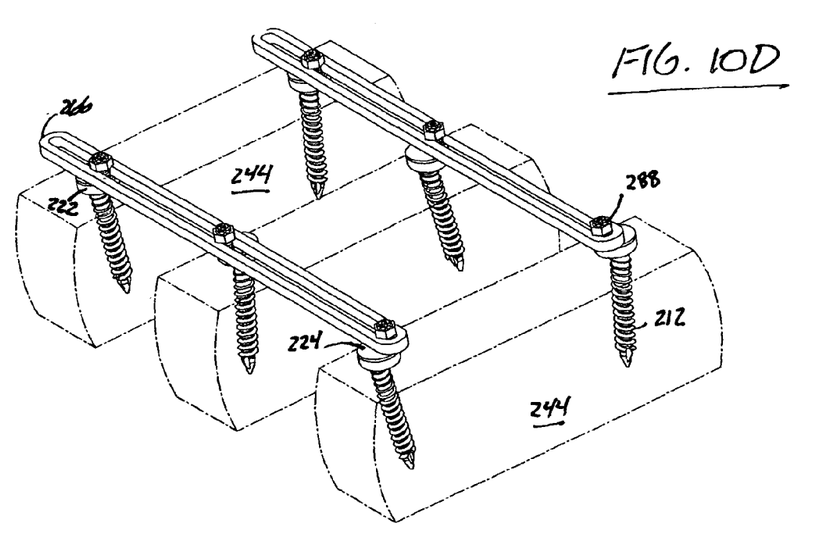

The plates 266 are then assembled to the screw caps 214 by placing the upright risers 241 of each screw cap 214 through the longitudinal slot 272 in each plate 266 as shown in FIG.

10C. As noted above, the reason that the risers 241 are offset from the bores 228 through which the heads 220 of screws 212 are received becomes apparent from the fact that the plate 266 is straight whereas the pedicle screws 212 are placed at different locations on the vertebral bodies as required by the particular pathology and/or shape and conformation of the patient's spinal column. Because the plate 266 cannot be bent to align the plate with the heads of the pedicle screws 212 in the manner that the rods 42 are bent as described above in connection with the embodiment shown in FIGS. 1-3, screw caps 214 are rotated on the heads 220 of pedicle screws 212 as needed to bring the risers 241 into alignment with the plate 266. Although not shown in FIG. 10C, as noted above in connection with the description of FIG. 3, the pedicle screws are positioned at different heights depending upon the shape and relative position of the vertebral bodies, and if necessary, a threaded extension such as the extension 16 shown in FIGS. 1-3 may be needed to facilitate placement of the plate 266 over the riser 241 of one or more screw caps 214. The nuts 288 are then tightened on the threads 240 formed on risers 241 to cause the plate 266 to engage the surfaces 247 of each washer 224 and the surfaces 270 on the raised area 254 of washer 224 to engage the head 220 of screw 212 to resist relative movement of screw 212 as described above. If an extension was utilized to facilitate the tightening of the nut 288 down onto the plate 266, the extension is then removed in the manner described above in connection with FIG. 2E.

Referring now to FIG. 11, yet another embodiment of an apparatus for incremental alignment of the spine that is constructed in accordance with the teachings of the present invention is shown and FIG. 11 is again numbered with reference numerals corresponding to the reference numerals used in FIGS. 1-10 but preceded by a "3." The embodiment 310 is assembled without a washer such as the washer 24, 124, or 224 shown in FIGS. 1-10 and the plate 366 bears directly against the top surface of the head 320 of pedicle screw 312 when nut 388 is tightened against the top surface of plate 366. Embodiment 310 is particularly useful, for instance, in surgeries in which the head 320 of pedicle screw 312 projects dorsally from the vertebral body (not shown in FIG. 11) to a height that would result in unacceptable dorsal extension if the additional height resulting from the use of a washer is added to the height of apparatus 310.

Those skilled in the art who have the benefit of this disclosure will recognize that certain changes can be made to the component parts of the apparatus of the present invention without changing the manner in which those parts function and/or interact to achieve their intended result. By way of example, those skilled in the art who have the benefit of this disclosure will recognize that depending upon the configuration of the spinal column of a particular patient, it may not be necessary to utilize the extensions 16 to align adjacent vertebrae. It will also be recognized by those skilled in the art that connector blocks (not shown) can be utilized so that transverse rods and/or plates can be connected to the longitudinal rods and/or plates of the apparatus of the present invention as needed for a particular surgical procedure as described in the specification of the above-incorporated application Ser. No. 12/148,006. All such changes, and others that will be clear to those skilled in the art from this description of the preferred embodiments of the invention, are intended to fall within the scope of the following, non-limiting claims.

What is claimed is:

1. A screw cap for use in an apparatus for aligning and/or stabilizing the spinal column comprising either a rod or a plate, a pedicle screw, and a nut for engaging the pedicle screw to affix the rod or plate thereto, the screw cap comprising:
    a base having a bore therethrough defining a cavity for receiving a head of a pedicle screw and a threaded riser formed thereon for receiving a threaded nut, the cavity and the head of a pedicle screw providing for cooperative screw cap retaining means that allows the head of the pedicle screw to enter the cavity from a cavity lower end opening and be retained in the cavity such that the base can be positioned in a plurality of positions relative to a longitudinal axis of the pedicle screw during surgical fixation, a longitudinal axis of the riser and a longitudinal axis of the bore in the base being laterally offset each other;
    a washer having a hole therethrough for receiving the riser formed on the base and a surface adapted for engagement by either a rod or a plate, movement of the rod or plate relative to the base being resisted when the threaded nut is tightened against the washer; and
    an extension configured to be releasably mounted on the riser being laterally offset from the longitudinal axis of the bore of the base, the riser having an intertnal and external threads, the extension comprising an unthreaded refresher gap and a threaded post located proximate the refresher gap,
        wherein the refresher gap is dimensioned to be slightly larger than the height of the threaded nut, and
        wherein the internal thread in the riser is configured to receive the threaded post while the external thread in the riser is configured to receive the the threaded nut.

2. The apparatus of claim 1, wherein the rod or plate bears against the head of the pedicle screw when the threaded nut is tightened with respect to the external thread in the riser.

3. The apparatus of claim 1, wherein the rod or plate is captured between the base and the washer when the threaded nut is tightened with respect to the external thread in the riser.

4. The apparatus of claim 1, additionally comprising a surface formed on either the base or the washer, or on both the base and the washer, for engaging the rod or plate.

5. The apparatus of claim 1, further comprising a surface formed on the washer for engaging the head of the pedicle screw when the threaded nut is tightened.

6. The apparatus of claim 1, further comprising a raised surface on the washer that is received in the bore in the base.

7. The apparatus of claim 6, wherein the raised surface on the washer engages the head of the pedicle screw to resist movement of the pedicle screw relative to the washer when the threaded nut is tightened.

8. The apparatus of claim 1, wherein the cooperative screw cap retaining means comprises complimentary threads, grooves, or a c-ring.

9. The apparatus of claim 8, wherein the diameter of the bore in the base is greater than the head of the pedicle screw received therein, allowing the pedicle screw to be oriented at any of a plurality of angles relative to the axis of the bore in the base.

10. The apparatus of claim 1, wherein either the washer or the base, or the washer and the base, are provided with complimentary-shaped surfaces for aligning the washer and the base when the threaded nut is tightened.

11. The apparatus of claim 1, wherein the washer is trapped between the base and the plate or rod when the threaded nut is tightened.

12. The apparatus of claim 1, wherein the surface formed on the washer for engaging either the rod or the plate is a concave surface adapted for engaging a rod and having a radius of curvature that approximates the diameter of the rod with the concave surface formed on the washer defining an arc that extend more than 180° around the diameter of the rod such that the washer upon engagement with respect to the rod retains to the rod as a slidable washer thereby favoring positioning of the washer for the aligning and/or stabilizing the spinal column.

* * * * *